US009345726B2

(12) United States Patent
Grazia et al.

(10) Patent No.: US 9,345,726 B2
(45) Date of Patent: May 24, 2016

(54) CD117+ CELLS AND USES THEREOF

(75) Inventors: Todd J. Grazia, Denver, CO (US);
Martin R. Zamora, Golden, CO (US);
Robert J. Plenter, Centennial, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/394,625

(22) PCT Filed: Sep. 7, 2010

(86) PCT No.: PCT/US2010/048021
§ 371 (c)(1),
(2), (4) Date: Mar. 28, 2012

(87) PCT Pub. No.: WO2011/029102
PCT Pub. Date: Mar. 10, 2011

(65) Prior Publication Data
US 2012/0276061 A1 Nov. 1, 2012

Related U.S. Application Data

(60) Provisional application No. 61/240,289, filed on Sep. 7, 2009.

(51) Int. Cl.
*A61K 35/12* (2015.01)
*A61P 37/06* (2006.01)
*A61K 35/28* (2015.01)
*A61K 9/00* (2006.01)
*A61K 45/06* (2006.01)
*C12N 5/0789* (2010.01)
*C12N 5/0775* (2010.01)
*C12N 5/071* (2010.01)

(52) U.S. Cl.
CPC ............ *A61K 35/28* (2013.01); *A61K 9/0019* (2013.01); *A61K 45/06* (2013.01); *C12N 5/0647* (2013.01); *C12N 5/0663* (2013.01); *C12N 5/0692* (2013.01); *A61K 2035/122* (2013.01)

(58) Field of Classification Search
None
See application file for complete search history.

(56) References Cited

U.S. PATENT DOCUMENTS

| 6,165,785 A * | 12/2000 | Ogle et al. ........... 435/347 |
| 2005/0221482 A1 | 10/2005 | Buret et al. |
| 2008/0213228 A1 | 9/2008 | Edinger et al. |
| 2009/0155220 A1 | 6/2009 | Losordo et al. |

FOREIGN PATENT DOCUMENTS

WO 2009073594 6/2009
WO WO 2009/073594 A1 6/2009

OTHER PUBLICATIONS

Gandy, Kimberly L.; Weissman, Irving L.; "Tolerance of Allogeneic Heart Grafts in Mice Simultaneously Reconstituted with Purified Allogeneic Hematopoietic Stem Cells" Transplantation, 65, 295-304, 1998.*
Fontes, Paulo; et al; "Bone marrow augmentation of donor-cell chimerism in kidney, liver, heart, and pancreas islet transplantation" The Lancet, 344, 151-155, 1994.*
Knoll, Greg A.; Bell, Robert C.; "Tacrolimus versus cyclosporin for immunosuppression in renal transplantation: meta-analysis of randomised trials" BMJ, 318, 1104-1107, 1999.*
Bonde, Sabrina; et al; "ES-Cell Derived Hematopoietic Cells Induce Transplantation Tolerance" PLoS ONE, 3, 1-10, 2008.*
Ikebukuro, Kazuya; et al; "Treatment of streptozotocin-induced diabetes mellitus by transplantation of islet cells plus bone marrow cells via portal vein in rats" Transplantation, 73, 512-518, 2002.*
Devine, Steven M; et al "Mesenchymal stem cells are capable of homing to the bone marrow of non-human primates following systemic infusion" Experimental Hematology, 29, 244-255, 2001.*
Burt, Richard K; et al "Treatment of Autoimmune Disease by Intense Immunosuppressive Conditioning and Autologous Hematopoietic Stem Cell Transplantation" Blood, 92, 3505-3514, 1998.*
Lagasse, Eric; et al; "Purified hematopoietic stem cells can differentiate into hepatocytes in vivo" Nature Medicine, 6, 1229-1234, 2000.*
Terai, Shuji, et al; "Improved Liver Function in Patients with Liver Cirrhosis After Autologous Bone Marrow Cell Infusion Therapy" Stem Cells, 24, 2292-2298, 2006.*
Fukami, Naohiko; et al; "Antibodies to MHC Class I Induce Autoimmunity: Role in the Pathogenesis of Chronic Rejection" The Journal of Immunology, 182, 309-318, 2009.*
Copelan, Edward A; "Hematopoietic Stem-Cell Transplantation" The New England Journal of Medicine, 354, 1813-1826, 2006.*
Alexander, S. I., N. Smith, M. Hu, D. Verran, A. Shun, S. Dorney, A. Smith, B. Webster, P. J. Shaw, A. Lammi, and M. O. Stormon, "Chimerism and tolerance in a recipient of a deceased-donor liver transplant," N Engl J Med, 2008, 358:369-374.
Soiffer, R, "Immune modulation and chronic graft-versus-host disease," Bone Marrow Transplant, 2008, 42 Suppl 1: S66-S69.

(Continued)

*Primary Examiner* — Renee Claytor
*Assistant Examiner* — David Berke-Schlessel
(74) *Attorney, Agent, or Firm* — Don D. Cha; Hamilton DeSanctis & Cha, LLP

(57) ABSTRACT

The present invention provides compositions comprising CD117+ cells and methods for using the same in allograft. In some aspects of the invention, methods are provided for prolonging allograft survival in a subject by administering CD117+ cells.

16 Claims, 5 Drawing Sheets

(56) References Cited

OTHER PUBLICATIONS

Li, F. X., J. W. Zhu, J. S. Tessem, J. Beilke, M. Varella-Garcia, J. Jensen, C. J. Hogan, and J. Degregori, "The development of diabetes in E2f1/E2f2 mutant mice reveals important roles for bone marrow-derived cells in preventing islet cell loss," Proceedings of the National Academy of Sciences of the United States of America, 2003, 100:12935-12940.

Li T.S., et al. 'CD117+ stem cells play a key role in therapeutic angiogenesis induced by bone marrow cell implantation', Am J Physiol Heart Circ Physiol., Sep. 2003, vol. 285(3), pp. H931-H937.

Taylor, D. O., J. Stehlik, L. B. Edwards, P. Aurora, J. D. Christie, F. Dobbels, R. Kirk, A. Y. Kucheryavaya, A. O. Rahmel, and M. I. Hertz, "Registry of the International Society for Heart and Lung Transplantation: Twenty-sixth Official Adult Heart Transplant Report—2009," J Heart Lung Transplant 2009, 28:1007-1022.

Johnson, M. R., K. H. Meyer, J. Haft, D. Kinder, S. A. Webber, and D. B. Dyke, "Heart transplantation in the United States, 1999-2008," Am J Transplant 2010, 10:1035-1046.

Burt, R. K., Y. Loh, W. Pearce, N. Beohar, W. G. Barr, R. Craig, Y. Wen, J. A. Rapp, and J. Kessler, "Clinical applications of blood-derived and marrow-derived stem cells for nonmalignant diseases," JAMA, 2008, 299: 925-936.

Dimmeler, S., J. Burchfield, and A. M. Zeiher, "Cell-based therapy of myocardial infarction," Arterioscler Thromb Vasc Biol, 2008, 28:208-216.

Kawamoto, A., and D. W. Losordo, "Endothelial progenitor cells for cardiovascular regeneration," Trends Cardiovasc Med, 2008, 18:33-37.

Bertolini, F., P. Mancuso, Y. Snaked, and R. S. Kerbel, "Molecular and cellular biomarkers for angiogenesis in clinical oncology," Drug Discov Today 2007, 12:806-812.

Shi, Q., S. Rafii, M. H. Wu, E. S. Wijelath, C. Yu, A. Ishida, Y. Fujita, S. Kothari, R. Mohle, L. R. Sauvage, M. A. Moore, R. F. Storb, and W. P. Hammond, "Evidence for circulating bone marrow-derived endothelial cells," Blood 1998, 92:362-367.

Bhattacharya, V., P. A. McSweeney, Q. Shi, B. Bruno, A. Ishida, R. Nash, R. F. Storb, L. R. Sauvage, W. P. Hammond, and M. H. Wu, "Enhanced endothelialization and microvessel formation in polyester grafts seeded with CD34(+) bone marrow cells," Blood 2000, 95:581-585.

Stump, M. M., G. L. Jordan, Jr., M. E. Debakey, and B. Halpert, "Endothelium Grown from Circulating Blood on Isolated Intravascular Dacron Hub," Am J Pathol, 1963, 43:361-367.

Wu, M. H., Q. Shi, A. R. Wechezak, A. W. Clowes, I. L. Gordon, and L. R. Sauvage, "Definitive proof of endothelialization of a Dacron arterial prosthesis in a human being," J Vase Surg, 1995, 21:862-867.

Grazia, T. J., B. A. Pietra, Z. A. Johnson, B. P. Kelly, R. J. Plenter, and R. G. Gill, "A two-step model of acute CD4 T-cell mediated cardiac allograft rejection," J Immunol, 2004, 172:7451-7458.

Hirschi, K. K., D. A. Ingram, and M. C. Yoder, "Assessing identity, phenotype, and fate of endothelial progenitor cells," Arterioscler Thromb Vase Biol, 2008, 28:1584-1595.

Yoder, M. C., L. E. Mead, D. Prater, T. R. Krier, K. N. Mroueh, F. Li, R. Krasich, C. J. Temm, J. T. Prchal, and D. A. Ingram, "Redefining endothelial progenitor cells via clonal analysis and hematopoietic stem/progenitor cell principals," Blood 2007, 109:1801-1809.

Lyman, S. D., and S. E. Jacobsen, c-kit ligand and Flt3 ligand: stem/progenitor cell factors with overlapping yet distinct activities. Blood, 1998, 91:1101-1134.

Rohde, E., C. Malischnik, D. Thaler, T. Maierhofer, W. Linkesch, G. Lanzer, C. Guelly, and D. Strunk, "Blood monocytes mimic endothelial progenitor cells. Stem Cells," 2006, 24:357-367.

Zhang, S. J., H. Zhang, Y. J. Wei, W. J. Su, Z. K. Liao, M. Hou, J. Y. Zhou, and S. S. Hu, "Adult endothelial progenitor cells from human peripheral blood maintain monocyte/macrophage function throughout in vitro culture," Cell Res, 2006, 16:577-584.

Rehman, J., J. Li, C. M. Orschell, and K. L. March, "Peripheral blood "endothelial progenitor cells" are derived from monocyte/macrophages and secrete angiogenic growth factors," Circulation, 2003, 107:1164-1169.

Rohde, E., C. Bartmann, K. Schallmoser, A. Reinisch, G. Lanzer, W. Linkesch, C. Guelly, and D. Strunk, "Immune cells mimic the morphology of endothelial progenitor colonies in vitro," Stem Cells, 2007, 25:1746-1752.

De Palma, M., M. A. Venneri, R. Galli, L. Sergi Sergi, L. S. Politi, M. Sampaolesi, and L. Naldini, "Tie2 identifies a hematopoietic lineage of proangiogenic monocytes required for tumor vessel formation and a mesenchymal population of pericyte progenitors," Cancer Cell, 2005, 8:211-226.

Zentilin, L., S. Tafuro, S. Zacchigna, N. Arsic, L. Pattarini, M. Sinigaglia, and M. Giacca, "Bone marrow mononuclear cells are recruited to the sites of VEGF-induced neovascularization but are not incorporated into the newly formed vessels," Blood, 2006, 107:3546-3554.

Jin, D. K., K. Shindo, H. G. Kopp, I. Petit, S. V. Shmelkov, L. M. Young, A. T. Hooper, H. Amano, S. T. Avecilla, B. Heissig, K. Hattori, F. Zhang, D. J. Hicklin, Y. Wu, Z. Zhu, A. Dunn, H. Salari, Z. Werb, N. R. Hackett, R. G. Crystal, D. Lyden, and S. Rafii, "Cytokine-mediated deployment of SDF-1 induces revascularization through recruitment of CXCR4+ hemangiocytes," Nat. Med, 2006, 12:557-567.

You, D., L. Waeckel, T. G. Ebrahimian, O. Blanc-Brude, P. Foubert, V. Barateau, M. Duriez, S. Lericousse-Roussanne, J. Vilar, E. Dejana, G. Tobelem, B. I. Levy, and J. S. Silvestre, "Increase in vascular permeability and vasodilation are critical for proangiogenic effects of stem cell therapy," Circulation, 2006, 114:328-338.

Rafii, S., and D. Lyden, "Cancer. A few to flip the angiogenic switch," Science, 2008, 319:163-164.

Anghelina, M., P. Krishnan, L. Moldovan, and N. I. Moldovan, "Monocytes/macrophages cooperate with progenitor cells during neovascularization and tissue repair: conversion of cell columns into fibrovascular bundles," Am J Pathol, 2006, 168:529-541.

Sood, R., S. Kalloway, A. E. Mast, C. J. Hillard, and H. Weiler, "Fetomaternal cross talk in the placental vascular bed: control of coagulation by trophoblast cells," Blood, 2006, 107:3173-3180.

Davie, N. J., J. T. Crossno, Jr., M. G. Frid, S. E. Hofmeister, J. T. Reeves, D. M. Hyde, T. C. Carpenter, J. A. Brunetti, I. K. McNiece, and K. R. Stenmark, "Hypoxia-induced pulmonary artery adventitial remodeling and neovascularization: contribution of progenitor cells," Am J Physiol Lung Cell Mol Physiol, 2004, 286:L668-678.

Reyes, M., A. Dudek, B. Jahagirdar, L. Koodie, P. H. Marker, and C. M. Verfaillie, "Origin of endothelial progenitors in human postnatal bone marrow," The Journal of clinical investigation, 2002, 109:337-346.

Young, H. E., T. A. Steele, R. A. Bray, J. Hudson, J. A. Floyd, K. Hawkins, K. Thomas, T. Austin, C. Edwards, J. Cuzzourt, M. Duenzl, P. A. Lucas, and A. C. Black, Jr, "Human reserve pluripotent mesenchymal stem cells are present in the connective tissues of skeletal muscle and dermis derived from fetal, adult, and geriatric donors," Anat Rec, 2001, 264:51-62.

Orlic, D., J. Kajstura, S. Chimenti, F. Limana, I. Jakoniuk, F. Quaini, B. Nadal-Ginard, D. M. Bodine, A. Leri, and P. Anversa, "Mobilized bone marrow cells repair the infarcted heart, improving function and survival," Proceedings of the National Academy of Sciences of the United States of America, 2001, 98:10344-10349.

Sata, M., A. Saiura, A. Kunisato, A. Tojo, S. Okada, T. Tokuhisa, H. Hirai, M. Makuuchi, Y. Hirata, and R. Nagai, "Hematopoietic stem cells differentiate into vascular cells that participate in the pathogenesis of atherosclerosis," Nat Med, 2002, 8:403-409.

Crossno, J. T., Jr., S. M. Majka, T. Grazia, R. G. Gill, and D. J. Klemm, "Rosiglitazone promotes development of a novel adipocyte population from bone marrow-derived circulating progenitor cells," The Journal of clinical investigation, 2006, 116:3220-3228.

Ogawa, M., S. Nishikawa, K. Yoshinaga, S. Hayashi, T. Kunisada, J. Nakao, T. Kina, T. Sudo, H. Kodama, and S. Nishikawa, "Expression and function of c-Kit in fetal hemopoietic progenitor cells: transition from the early c-Kit-independent to the late c-Kit-dependent wave of hemopoiesis in the murine embryo," Development, 1993, 117:1089-1098.

(56) References Cited

OTHER PUBLICATIONS

Laing, A. J., J. P. Dillon, E. T. Condon, J. C. Coffey, J. T. Street, J. H. Wang, A. J. McGuinness, and H. P. Redmond, "A systemic provascular response in bone marrow to musculoskeletal trauma in mice," J Bone Joint Surg Br, 2007, 89:116-120.

Patschan, D., K. Krupincza, S. Patschan, Z. Zhang, C. Hamby, and M. S. Goligorsky, "Dynamics of mobilization and homing of endothelial progenitor cells after acute renal ischemia: modulation by ischemic preconditioning," Am J Physiol Renal Physiol, 2006, 291:F176-185.

Dentelli, P., A. Rosso, A. Balsamo, S. Colmenares Benedetto, A. Zeoli, M. Pegoraro, G. Camussi, L. Pegoraro, and M. F. Brizzi, "C-Kit, by interacting with the membrane-bound ligand, recruits endothelial progenitor cells to inflamed endothelium," Blood, 2007, 109:4264-4271.

Lupatov, A. Y., P. A. Karalkin, Y. G. Suzdal'Tseva, V. V. Burunova, V. N. Yarygin, and K. N. Yarygin, "Cytofluorometric analysis of phenotypes of human bone marrow and umbilical fibroblast-like cells," Bulletin of experimental biology and medicine, 2006, 142:521-526.

Martin-Rendon, E., D. Sweeney, F. Lu, J. Girdlestone, C. Navarrete, and S. M. Watt, "5-Azacytidine-treated human mesenchymal stem/progenitor cells derived from umbilical cord, cord blood and bone marrow do not generate cardiomyocytes in vitro at high frequencies," Vox sanguinis, 2008, 95:137-148.

Shih, Y. R., T. K. Kuo, A. H. Yang, O. K. Lee, and C. H. Lee, "Isolation and characterization of stem cells from the human parathyroid gland," Cell proliferation, 2009, 42:461-470.

Casiraghi, F., N. Azzollini, P. Cassis, B. Imberti, M. Morigi, D. Cugini, R. A. Cavinato, M. Todeschini, S. Solini, A. Sonzogni, N. Perico, G. Remuzzi, and M. Noris, "Pretransplant infusion of mesenchymal stem cells prolongs the survival of a semiallogeneic heart transplant through the generation of regulatory T cells," J Immunol, 2008, 181:3933-3946.

Ge, W., J. Jiang, M. L. Baroja, J. Arp, R. Zassoko, W. Liu, A. Bartholomew, B. Garcia, and H. Wang, "Infusion of mesenchymal stem cells and rapamycin synergize to attenuate alloimmune responses and promote cardiac allograft tolerance," Am J Transplant, 2009, 9:1760-1772.

Grazia, T. J., R. J. Plenter, S. M. Weber, H. M. Lepper, F. Victorino, M. R. Zamora, B. A. Pietra, and R. G. Gill, "Acute cardiac allograft rejection by directly cytotoxic CD4 T cells: parallel requirements for Fas and perforin," Transplantation, 2010, 89:33-39.

Grazia, T. J., R. J. Plenter, A. N. Doan, B. P. Kelly, S. M. Weber, J. S. Kurche, S. O. Cushing, R. G. Gill, and B. A. Pietra, "Spontaneous allograft tolerance in B7-deficient mice independent of preexisting endogenous CD4+CD25+ regulatory T-cells," Transplantation, 2007, 83:1449-1458.

Corry, R. J., H. J. Winn, and P. S. Russell, "Primarily vascularized allografts of hearts in mice. The role of H-2D, H-2K, and non-H-2 antigens in rejection," Transplantation, 1973, 16:343-350.

Schaefer, B. C., M. L. Schaefer, J. W. Kappler, P. Marrack, and R. M. Kedl, "Observation of antigen-dependent CD8+ T-cell/dendritic cell interactions in vivo," Cell Immunol, 2001, 214:110-122.

Li, X. C., D. M. Rothstein, and M. H. Sayegh, "Costimulatory pathways in transplantation: challenges and new developments," Immunological reviews, 2009, 229:271-293.

Zhang, G. Y., M. Hu, Y. M. Wang, and S. I. Alexander, "Foxp3 as a marker of tolerance induction versus rejection," Current opinion in organ transplantation, 2009, 14:40-45.

Sagoo, P., G. Lombardi, and R. I. Lechler, "Regulatory T cells as therapeutic cells," Current opinion in organ transplantation, 2008, 13:645-653.

Balner, H, Persistence of Tolerance Towards Donor-Type Antigens after Temporary Chimerism in Rats. Transplantation, 1964, 2:464-474.

Kawai, T., A. B. Cosimi, T. R. Spitzer, N. Tolkoff-Rubin, M. Suthanthiran, S. L. Saidman, J. Shaffer, F. I. Preffer, R. Ding, V. Sharma, J. A. Fishman, B. Dey, D. S. Ko, M. Hertl, N. B. Goes, W. Wong, W. W. Williams, Jr., R. B. Colvin, M. Sykes, and D. H. Sachs, "HLA-mismatched renal transplantation without maintenance immunosuppression," N Engl J Med, 2008, 358:353-361.

Scandling, J. D., S. Busque, S. Dejbakhsh-Jones, C. Benike, M. T. Millan, J. A. Shizuru, R. T. Hoppe, R. Lowsky, E. G. Engleman, and S. Strober, "Tolerance and chimerism after renal and hematopoietic-cell transplantation," N Engl J Med, 2008, 358:362-368.

Li T.S. et al., CD117+ Stem Cells Play a Key Role in Therapeutic Angiogenesis Induced by Bone Marrow Cell Implantation, Am J Physiol Heart Circ Physiol., vol. 285, No. 3, Sep. 2003, pp. H931-H937.

Bearzi Claudia et al, "Human cardiac stem cells," Proceedings of the national academy of sciences, Aug. 1, 2007, 14068-14073, vol. 104 No. 35.

Fazel Shafie et al, "Cardioprotective c-kit(+) cells are from the bone marrow and regulate the myocardial balance of angiogenic cytokines," Journal of clinical investigation, Jul. 2006, 1865-1877, vol. 116 No. 7.

\* cited by examiner

CD117+ CELLS AND USES THEREOF

CROSS-REFERENCE TO RELATED APPLICATIONS

This application claims the priority benefit of U.S. Provisional Application No. 61/240,289, filed Sep. 7, 2009, which is incorporated herein by reference in its entirety.

STATEMENT REGARDING FEDERALLY FUNDED RESEARCH

This invention was made with government support under grant number HL077503 awarded by the National Institutes of Health. The government has certain rights in the invention.

FIELD OF THE INVENTION

The present invention relates compositions comprising CD117+ cells and methods for using the same in allograft.

BACKGROUND OF THE INVENTION

The success of surgical transplantation of organs and tissue is largely dependent on the ability of the clinician to modulate the immune response of the transplant recipient. Specifically, the immunological response directed against the transplanted foreign tissue must be controlled if the tissue is to survive and function. It is known that the normally functioning immune system of the transplant recipient recognizes the transplanted organ as "non-self" tissue and thereafter mounts an immune response to the presence of the transplanted organ. Left unchecked, the immune response will generate a multitude of cells and proteins that will ultimately result in the loss of biological functioning or the death of the transplanted organ.

Transplant rejection remains the leading impediment to long term graft survival in humans. Currently, tissue and organ transplant recipients are typically treated with one or more cytotoxic agents in an effort to suppress the transplant recipient's immune response against the transplanted organ or tissue. For example, cyclosporin A, a cyclic peptide consisting of 11 amino acid residues and produced by the fungus species *Tolypocladium Inflatum* Gams is currently used to administer to the recipients of kidney, liver, pancreas and heart allografts (i.e., wherein donor and recipient are of the same species). However, administration of cyclosporin A is not without drawbacks as the drug can cause kidney and liver toxicity as well as hypertension. Moreover, the use of cyclosporin A can lead to malignancies (such as lymphoma) and lead to opportunistic infection due to the systemic immunosuppression it induces in patients receiving long term treatment with the drug, i.e., the normal protective immune response of the host to pathogenic microorganisms is down-regulated thereby increasing the risk of infections caused by such microorganisms.

Currently available immunosuppressive agents such as cyclosporin A fail to prevent either acute or chronic refractory rejection. It is estimated that nearly 20% of cadaver kidney and cardiac grafts are lost during the first year post-transplant, primarily due to acute rejection. Chronic rejection poses formidable hurdles for extant immunosuppressant therapies. Studies have shown that 50% of lung transplant recipients develop bronchitis obliterans, the hallmark of chronic allograft rejection. Some studies have shown that only 20% of cadaver renal transplants continue to function at ten years post-transplant. Transplant vasculopathy, induced by chronic rejection and ischemia, is the leading cause of cardiac transplant graft loss after the first year post transplant. Moreover, current post-transplantation therapy requires continuous (e.g., daily) administration of an anti-rejection agent for the duration of the transplant recipient's life.

Therefore, there is a continuing need for new methods for improving the transplantation outcome in a mammalian cell, tissue, or organ transplant recipient.

SUMMARY OF THE INVENTION

Some aspects of the invention provide methods for improving the transplantation outcome in a mammalian cell, tissue, or organ transplant recipient. Such methods include administering to said mammalian transplant recipient a therapeutically effective amount of CD117+ cells. In some embodiments, CD117+ cells comprise CD117+ progenitor cells, CD117+ stem cells, or a mixture thereof. Within these embodiments, in some instances CD117+ cells are autologous CD117+ progenitor cells. In some cases, autologous CD117+ progenitor cells are bone marrow derived autologous CD117+ progenitor cells. In other embodiments, CD117+ cells are CD45+CD117+ cells.

Still in other embodiments, the improvement in transplantation outcome is reduced graft rejection. In some instances, the reduced graft rejection is reduced chronic graft rejection. While in other instances, the reduced graft rejection is reduced acute graft rejection.

Yet in other embodiments, the improvement in transplantation outcome is increased graft survival.

Methods of the invention can be used in an allograft or a xenograft.

Typically, the mammalian transplant recipient is human.

While methods of the invention can be used in any type of cell, tissue and organ transplantation, in some embodiments, the transplantation comprises transplantation of heart, islet cells, kidney, liver, lung, pancreas, skin, ocular, intestine, or a combination thereof.

In one particular embodiments, the transplantation comprises islet cell grafting. In some instances of this embodiment, the number of islet cells transplanted is less than the number of islet cells transplanted in the absence of CD117+ cells.

Methods of the invention can also include administering a therapeutically effective amount of an immunosuppressive agent to said mammalian transplant recipient. In such embodiments, the therapeutically effective amount of said immunosuppressive agent is typically reduced as compared to a therapeutically effective amount of the immunosuppressive agent when used alone. Exemplary immunosuppressive agents that are suitable in such embodiments include cyclosporin A, rapamycin, FK501, mycophenolate mofetil, azathioprine, deoxyspergualin, FK506 (tacrolimus), cytoxan (cyclophosphamide), everolimus, glucocorticoid steroids (prednisone/solumedrol), and a combination thereof. In one particular embodiment, the immunosuppressive agent is a cyclic peptide produced by the fungus species *Tolypocladium Inflatum* Gams such as cyclosporin A.

In some embodiments, improvement in transplantation outcome is decreased lymphocytic infiltration, vasculitis, infarction, ischemia, thrombosis, intimal thickening, glomerular atrophy, glomerular sclerosis, tubular atrophy, hyalinization, interstitial fibrosis, cortical fibrosis, serum creatinine levels, intimal proliferation, hypertrophy, cardiac vessel disease post-transplant, graft intimal hyperplasia, luminal occlusion, or bronchitis obliterans.

CD117+ cells can be co-transplanted, administered systemically or a combination thereof. Often CD117+ cells are also administered post-transplantation at various intervals.

Other aspects of the invention provide isolated cell compositions comprising at least about 60% of CD117+ cells. In some embodiments, the composition comprise at least about 60%, typically at least about 80%, and often at least about 90%, of CD117+ progenitor cells. Still in other embodiments, CD117+ progenitor cells are bone marrow derived CD117+ progenitor cells. Yet in other embodiments, at least about 60%, typically at least about 80%, and often at least about 90%, of CD117+ cells are CD45+CD117+ cells.

BRIEF DESCRIPTION OF THE DRAWINGS

FIG. 4A: Unmanipulated freshly harvested host-type B6 bone marrow cells (BM), host-type B6 CD117$^-$ Effluent (Eff), and host-type B6 CD117$^+$ progenitor cells (PC) were added to standard B6 responder (R)+BALB/c stimulator (S) cultures at 1:1 with responders. Results demonstrate equivalent inhibition of T-cell proliferation by BM, Eff, and PC (p<0.0001 for BM, Eff, and PC vs. positive control R+S culture, unpaired T-test). Error bars represent the standard deviation from quadruplicate wells in the MLR assay. The experiment above was repeated a minimum of 3 times with the current figure representing one typical result. FIG. 4B: Freshly harvested host-type B6 CD117$^-$ effluent and host-type B6 CD117$^+$ progenitor cells (PC) were added to standard B6 responder (R)+BALB/c stimulator (S) cultures at 1:1-1:256 with responders (1:1-1:64 shown). Results are expressed as a percent of positive control (R+S) proliferation and demonstrate significant inhibition of proliferation by both CD117$^+$ PC and CD117$^-$ effluent out to a ratio of 1:16 (p<0.005 in all cases, unpaired T-test). Additionally, CD117$^+$ PC inhibited T-cell proliferation significantly better than CD117$^-$ effluent out to a dilution of 1:2 (p<0.0002, unpaired T-test). Error bars represent the standard deviation from quadruplicate wells in the MLR assay. The experiment above was repeated 3 times with the current figure representing one typical result.

DETAILED DESCRIPTION OF THE INVENTION

Figure 1:
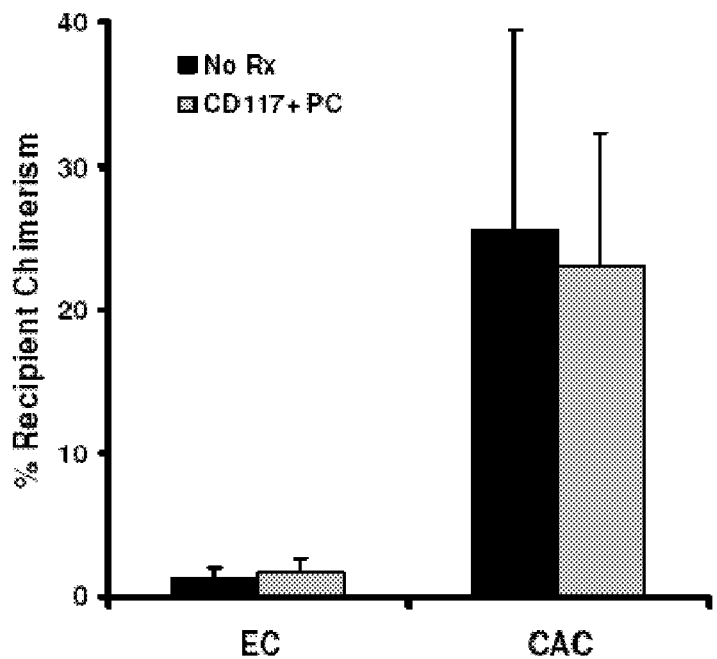
FIG. 1 is a graph showing the result of vascular cell chimerism in CD117+PC treated and untreated allografts.

Following Abbreviations are used: PC—progenitor cells, EPC—endothelial progenitor cell, CAC—circulating angiogenic cell, MSC—mesenchymal stem cells, BM—bone marrow, CNI—calcineurin inhibitor, APC—antigen presenting cell, MLN—mesenteric lymph nodes, SPL—spleen, EC—endothelial cell.

Transplant rejection is characterized by an acute or chronic diminution in the physiological function of a transplanted organ. Such diminuation in function is measured by biological factors specific to the organ transplanted. For example, for kidney transplant rejection assessment, increased glomerular atrophy, intimal thickening, tubular atrophy, interstitial fibrosis, lymphocyte infiltration and cortical scarring independently or taken together are indicators of graft rejection. Similarly, for heart transplant rejection assessment, increased cardiac vessel disease post-transplant, and increased graft intimal hyperplasia independently or taken together are indicators of graft rejection.

It is believed that acute rejection is mainly T-cell activated. The role of inflammation has also been recently implicated in the pathogenesis of rejection. Studies have shown that activation of many cytokines (e.g., IL-2, IFNυ, TNFα) and chemokines (e.g., RANTES, IL-8, MCP-1 and MIP-1α) occurs during inflammatory responses to graft rejection. It is believed that decreasing initial inflammation can lead to lower acute and long term rejection rates and improved graft function.

Chronic rejection is less well understood. Historically, chronic vascular rejection has been described as repetitive endothelial injury leading to intimal proliferation, hypertrophy and subsequent luminal occlusion. Some researchers have proposed inflammatory, humoral, cellular, and cytokine-related non-specific scarring mechanisms as etiologies of chronic rejection. It is now known that alloantigen-independent factors play an essential role in chronic rejection. For example, some studies have shown that human kidney grafts from identical twins lose their grafts at ten years. These isograft losses are believed to be a consequence of injury during preservation and reperfusion. Injury from multiple etiologies activates thrombotic and inflammatory cascades in the vascular wall that converge, initiating a rapid pervasive response which stimulates cellular migration, invasion and proliferation at sites of vessel injury. As a result, inflammatory mediators and cytokines are upregulated and secreted in response to endothelial injury, which results in the accumulation of macrophages that, in turn, upregulate more chemokines (e.g., RANTES, IL-8, MCP-1 and MIP-1α).

Cardiac transplantation continues to be the only viable option for majority of patients with end-stage cardiomyopathy. Despite the use of mandatory non-specific immunosuppression, acute and chronic allograft rejection remain major causes of morbidity and mortality with survival being 50-56% at 10 years and 20% at 20 years. Unfortunately, use of non specific immunosuppression leads to further morbidity and mortality from infection, malignancy, hypertension, diabetes and renal failure. Accordingly, new therapeutic modalities are needed to improve survival and to diminish reliance on non-specific immunosuppressants with their associated morbidities.

An area of increasing interest over the past decade has been that of progenitor cell (PC) involvement in neo-angiogenesis and tissue repair/remodeling. Progenitor cell therapy—with hematopoietic progenitor cells (HPC), mesenchymal stem cells (MSC), or endothelial progenitor cells (EPC)—has been applied to areas such as myocardial infarction and ischemia-related injury. Results appear to demonstrate significant benefit. More recent data suggest that certain HPC (circulating angiogenic cells or 'CAC'), as well as MSC, may possess immune regulatory properties. Additionally, host-type PC-derived endothelial cells (EC) or CAC could potentially serve to repair damaged blood vessels by directly replacing the critical donor EC with a source of 'self' cells. More recently, there has been an interest in the area of donor-derived bone marrow cell-therapy in solid organ transplantation, with reports of tolerance induction via "mixed chimerism" in humans. However, donor-derived therapy is highly problematic in that the risk of potentially fatal graft versus host disease is high and the ability to harvest donor-specific bone marrow prior to transplantation is limited.

Relevance to transplantation is the finding that the allograft endothelial cell (EC) is likely the target of acute CD4 T-cell mediate rejection, making modification of donor EC a candidate means of abrogating acute rejection. Currently, no clear EPC-specific marker exists. However, Yoder and coworkers have defined an EPC as $CD34^+$, $CD45^-$, $CD31^+$, $CD133^-$, $CD14^-$, $CD115^-$, $VEGFR2^+$, and positive for other EC markers such as vWF and eNos. See, for example, Hirschi et al., *Arterioscler Thromb Vasc Biol.*, 2008, 28, 1584-1595; and Yoder et al., *Blood*, 2007, 109, 1801-1809.

There exists a subset of monocytic cells expressing high levels of EC markers, thought previously to represent EPC, termed Circulating Angiogenic Cells (CAC). These cells are believed to be hematopoietic progenitor-derived co-expressing CD45, CD11b, CD11c, CD14, and CD68 and have shown to ingest bacteria in vitro. Importantly, these cells have been shown to contribute to neo-angiogenesis, local vascular remodeling, and may incorporate into vessels as 'EC-like' cells. Additionally, other bone marrow-derived progenitor cells (PC) identified by the cell surface marker c-kit, give rise to EC, smooth muscle cells, adipocytes, and hematopoietic cells. C-kit is a transmembrane tyrosine kinase receptor (CD117) for stem cell factor that is mobilized from the bone marrow and tracks to atherosclerotic lesions, sites of cardiac infarct, and areas of ischemic injury. $C-kit^+$ cells contain cellular sub-populations that have the potential to give rise to EPC and CAC and c-kit expression on PC is critical for homing to injured vasculature during neo-angiogenesis. $C-kit^+$ PC are in direct contrast to MSC, which are $CD117^-$ $CD45^-$. To date, primary autologous MSC therapy has been relatively ineffectual in promoting allograft survival, as long-term acceptance has only been established under semi-allogeneic conditions or with concomitant immune-suppressive therapy.

Some aspects of the invention is based on the discovery by the present inventors that autologous $CD117^+PC$ do not significantly increase recipient EC chimerism, but they do attenuate acute allograft rejection in a dose-dependent manner. In addition, the present inventors have discovered that $CD117^+PC$ inhibit T-cell allo-proliferation in vitro via a primary paracrine mechanism, and to appear to dampen late T-cell responsiveness when re-stimulated ex-vivo. $CD117^+$ PC represent a unique population, distinct from MSC, and as such represent a novel autologous therapy.

The present inventors have also discovered that surprisingly and unexpectedly CD117+ cells (e.g., a CD117+ cell enriched composition) can be used to treat transplant rejection. For purposes of the present invention, the terms "treat", "treating" and "treatment" include preventing, inhibiting, reducing, the occurrence of and/or ameliorating the physiological effects of graft rejection. By "graft rejection" is meant allograft and xenograft transplant rejection. Typically, CD117+ cells of the invention comprise CD117+ progenitor cells, CD117+ stem cells, or a mixture thereof. Often CD117+ cells of the invention are autologous CD117+ progenitor cells. In some embodiments, autologous CD117+ progenitor cells are bone marrow derived autologous CD117+ progenitor cells. Still in other embodiments, CD117+ cells are CD45+CD117+ cells.

Methods of the invention are useful in a wide variety of allotranplantation or allograft including, but not limited to, liver, skin, ocular, kidney, pancreas, islet cell, lung, as well as other cell, tissue, and organ transplantation or grafting. However, for the sake of clarity and brevity, methods of the invention will now be described in connection with cardiac and islet cell transplantation.

Some aspects of the invention provide isolated cell composition comprising CD117+ cells. It should be appreciated that such a composition can also include other non-cellular materials, such as, but not limited to, serum, buffer solution, electrolytes, cell nutrients, etc. Typically, at least 60% of the total cells of the isolated cell composition comprises CD117+ cells. Often at least 80% and more often at least 90% of the total cells of the isolated cell composition comprises CD117+ cells. In some embodiments, at least 60% of the total cells of the isolated cell composition of the invention is CD117+ progenitor cells. Often at least 80%, and more often at least 90%, of the total cells of the isolated cell composition of the invention is CD117+ progenitor cells. In other embodiments, at least 60% of the total cells of the isolated cell composition of the invention is bone marrow derived CD117+ progenitor cells. Often at least 80%, and more often at least 90%, of the total cells of the isolated cell composition of the invention is bone marrow derived CD117+ progenitor cells. Still in other embodiments, at least 60% of the total cells of the isolated cell composition of the invention is CD45+CD117+ cells. Often at least 80%, and more often at least 90%, of the total cells of the isolated cell composition of the invention is CD45+ CD117+ cells.

In some embodiments, methods of the invention can also include administering anti-rejection agent to the subject. The term "anti-rejection agent" means any commercially available immunosuppressive pharmaceutical agent which reduces the tendency of a transplanted organ to be rejected by the transplant recipient. Transplant rejection treatment is assessed in accordance with the present invention by one or more of the following organ-dependent parameters: decreased coronary graft intimal hyperplasia compared to control grafted vessels; renal function as measured by serial serum creatinine levels; graft survival prolongation; hyalinization and cortical scarring in renal grafts.

Anti-rejection agents in accordance with the invention are contemplated to include immunosuppressive agents. Anti-rejection agents contemplated by the present invention specifically include, but are not limited to, cyclosporin (e.g., Cyclosporin A, Sandimmune®, Neoral® (Novartis), Rapimmune® (American Home Products), FK501 (Fujisawa), CELLCEPT® (Roche, Syntex), IMUREK®, SPANIDIN® and PROGRAF®.

The term "subject" as used herein is taken to mean any mammalian patient to which the compositions of the invention may be administered. Subjects specifically intended for treatment with the compositions and methodologies of the present invention include humans, as well as non-human primates, sheep, horses, cattle, goats, pigs, dogs, cats, rabbits, guinea pigs, poultry, hamsters, rats and mice, as well as the organs, derived or originating from these hosts.

The CD117+ cells are delivered, for treating transplant rejection, in a manner consistent with conventional methodologies associated with transplantation of mammalian organs such as for example, intravenously, intra-articularly, intraperitoneally, intramuscularly, or subcutaneously. In some embodiments CD117+ cells are co-transplanted, administered systemically or a combination thereof.

Generally, CD117+ cells are administered to a human patient in a therapeutically effective amount. The term "therapeutically effective amount" means the dose needed to effectively treat the physiological effects of graft rejection. While a therapeutically effective amount of CD117+ cells various depending on the type of cell, tissue or organ transplanted, typically a therapeutically effective amount of CD117+ cells is at least about $10^4$ cells, often at least about $10^6$ cells, and more often at least about $10^7$ cells. It should be appreciated, however, the amount of CD117+ cells administered is not limited to these specific ranges and examples given herein. In fact, the number of CD117+ cells administered can vary widely depending on a variety of factors (e.g., age and size of the recipient, type of cells, tissue or organ transplanted, etc.) to treat transplantation rejection. For example, in some embodiments, a total cell dosage of $8 \times 10^6$ ($2 \times 10^6$ cells on days +1, +5, +9, and +15) and a total dosage of $4 \times 10^7$ ($10^7$ cells on days +1, +5, +9, and +15 post transplantation) are used.

Typically, CD117+ cells are administered at the time of transplantation or shortly thereafter. In some embodiments, CD117+ cells are also administered at various intervals after transplantation.

In some embodiments, methods of the invention can be used in islet cell transplantation. In such embodiments, methods of the invention significantly reduce the number of islet cells required for a successful transplantation. Islets are normally defined as islet 'equivalents' since they are quite heterogeneous in size. An islet equivalent is a 150 micron diameter islet and the number of total islet equivalents (IEQ) per kilogram is the usual definition of dosage. Typically, islet cell transplantation (which is typically used to treat diabetes) requires about 4,000 IEQ/kg or more in order to have a relatively successful transplantation rate. Methods of the invention can significantly reduce the number of IEQ required to have the same success rate. Typically, methods of the invention allow using about 4,000 IEQ/kg or less, often about 2,500 to about 4,000 IEQ/kg for a successful islet transplantation in human.

Methods of the invention significantly reduce the risk of graft versus host disease—a potentially fatal complication in solid organ transplant recipients—and allow cells to be harvested from patients awaiting transplantation, be expanded ex-vivo and cryopreserved for future use—something that is not feasible with donor-specific therapy. Methods of the invention result in a significant prolongation of allograft (and therefore patient) survival and/or immune ignorance or tolerance, thereby obviating the need for non-specific immunosuppressants and their associated morbidities.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

As disclosed herein, in vivo heart transplant experiments by the present inventors utilizing autologous CD117+ PC infusions showed statistically significant attenuation of acute cardiac rejection in a dose dependent fashion. Additional experiments showed that PC-derived cells were present within the allograft and that a large percentage of these cells co-expressed CD31 and CD45– indicating involvement by CAC. These data indicate a local immunomodulatory effect of the PC. The present inventors have discovered that autologous CD117+ PC therapy resulted in a prolonged cardiac allograft survival. Without being bound by any theory, it is believed that PC-derived monocyte subset CACs are acting to locally repair graft parenchymal and vascular cells as well as to locally inhibit the alloimmune response. At a threshold dose of PC a long term cardiac allograft acceptance can be achieved.

Results with autologous CD117+ PC demonstrated significant prolongation of allograft survival in a dose-dependent manner. In some instances, allograft prolongation of at least 3-5 times normal can be achieved with methods of the invention. Increasing the numbers of PC used can increase the potential local immunomodulatory effects of the PC on the allograft and/or lead to a larger number of recipient-derived (self) allograft vascular targets. Without being bound by any theory, it is believed that a threshold number of PC infused results in larger numbers of PC-derived cells within the allograft and to long term allograft acceptance.

It is also believed that PC-derived CAC are homing to and incorporating into the allograft in peri-vascular and intra-vascular/luminal locations. Data by the present inventors (not shown) suggest that the two likely cellular candidates involved in allograft prolongation are (i) ECs—via maturation of EPCs within the allograft or (ii) Monocytes/CACs of HPC origin that can act to promote local neo-angiogenesis via paracrine effects, that can potentially incorporate into damaged blood vessels as 'EC-like' cells, or that may have local immunomodulatory effects on the allograft. It is believed that the removal of PC-derived monocytes/CAC leads to substantially complete abrogation of allograft prolongation seen with autologous CD117+ PC therapy. It appears that PC-derived CAC act locally and systemically to inhibit the allo-immune response.

The present inventors have also observed a statistically significant in vivo prolongation of cardiac allograft survival in mice with intravenous CD117+ cell therapy given at the time of transplantation and at intervals after transplantation. Survival benefit was shown to be dose-dependent.

Mice

Female BALB/cByJ (BALB/c H-2$^d$) and C3H/HeJ (C3H, H-2$^k$) mice were used as heart transplant donors. Female C57BL/6ByJ (B6, H-2$^b$) and C57B6-Rag1$^{tm1/Mom}$ (B6 rag$^{-/-}$, H-2$^b$) mice were used as heart transplant recipients. Aged (12 mos) B6, BALB/c, UBI-GFP/BL6 (B6 gfp, H-2$^b$), and B6.5JL-Ptprc$^a$ Pepc$^b$/BoyJ (B6 CD45.1, H-2$^b$) mice were used as cell donors. All mice were purchased from The Jackson Laboratory (Bar Harbor, Me., USA). Animals were housed under pathogen-free conditions according to NIH guidelines.

CD117 Cell-Enrichment

Cell donor femurs, tibias, and humeri were aseptically removed from aged mice (12 mos old) and flushed with 1×HBSS and a 25-gauge needle. Cells were strained (70 μm), centrifuged (500 g for 5 min), and resuspended in 10 mL autoMACS Buffer with 5% BSA (Miltenyi). Cells were overlaid on Lympholyte-M (Cedarlane) and centrifuged at 800 g for 20 min. Cells were counted, resuspended at 80 μl/10$^7$ cells in autoMACS Buffer and incubated with anti-CD117 Micro-Beads (Miltenyi) for 15 min per manufacturer's protocol. Cells were rinsed, passed over a MidiMACS positive selection LS column (Miltenyi), rinsed, and run over a second column per manufacturer's protocol. Effluent cells were obtained via flow-through from the first column. Cells were kept at 4° C. at all times.

Flow Cytometry

Analysis was performed using a FACSCalibur cytometer (Becton Dickinson), with cell staining performed as described by the present inventor. See Grazia et al., in *J. Immunol.*, 2004, 172, 7451-7458. A 1:100 dilution of PE-CD25 (clone PC61), PerCP-CD4 (clone RM4-5), PerCP-CD8 (clone 53-6.7), APC/FITC-CD45.1 (clone A20), PE/APC-CD31 (clone 390), PE/PerCP-CD45 (clone 30-F11), FITC-H-2K$^b$ (clone AF6-88.5), PE-H-2K$^d$ (clone SF1-1.1), APC-CD117 (clone 3C1), and FITC-Foxp3 (clone FJK-16s, per eBioscience intra-cellular kit) was utilized.

Cardiac Digestion

Control and allograft hearts were digested for flow cytometric analysis as described by the present inventor. Id. Separated cells were prepared for flow cytometry as above.

Mixed Lymphocyte Reactions

Mixed lymphocyte reactions (MLR) with recipient-type B6 lymph node responder cells and BALB/c or C3H stimulator splenocytes were performed as previously by the present inventor. See Grazia et al., in *Transplantation*, 2010, 89, 33-39; and Grazia et al., in *Transplantation*, 2007, 83, 1449-1458. B6 CD117$^+$PC, B6 CD117$^-$ effluent cells, or B6 bone marrow cells were added (at 1:1-1:256 with responders). Differences within a given quadruplicate culture assay were assessed with the unpaired T-test via InStat statistical software.

In Vitro and In Vivo Proliferation Assays Using CFSE Cell Labeling

Single cell suspensions of RBC-depleted B6 CD45.1 splenocytes (5×10$^6$ cells/mL in 1×PBS+0.1% FCS) were CFSE-labeled in 5 mM carboxyfluorescein succinimidyl ester (CFSE) (1:2000) for 10 min at 37° C. Cells were washed twice with RPMI+20% FCS and resuspended in media (EMEM+10% FCS, 10$^{-5}$ M 2-Me, and antibiotics). CFSE-labeled splenocytes (2×10$^6$) in 0.3 mL of media were then added to the each main well of the transwell plate (CoStar, Cat#3422). Gamma-irradiated (2500 rads) BALB/c splenocytes (3×10$^6$) were then added to each main well in 0.15 mL of media. Media, 2×10$^6$ B6 CD117$^+$PC or 2×10$^6$ B6 CD117$^-$ effluent cells were added to the appropriate main wells in a total of 0.15 mL media. Finally, media, 2×10$^5$ B6 CD117$^+$PC, or 2×10$^5$ B6 CD117$^-$ effluent cells were added to the corresponding transwell in a total volume of 0.1 mL. CFSE-labeled B6 CD45.1$^+$ responders were harvested on day 4 for flow cytometry (CD45.1, CD4, CD8, and CFSE).

For tracking cell proliferation in vivo, CFSE labeling of B6 CD45.1 splenocytes was accomplished as above and 10$^7$ injected retro-orbitally (RO) on the day of transplantation (BALB/c→B6). On day +1, 10$^7$ B6 CD117$^+$PC, 10$^7$ B6 CD117$^-$ effluent cells, or no cells were injected RO. Heart-grafted mice were sacrificed on day +4 with harvest of the allograft, peripheral blood, mesenteric lymph nodes, and spleen for flow cytometry (CD45.1, CD4, CD8, and CFSE).

Cytokines and Antibodies

Recombinant transforming growth factor-β1 (R&D Systems, cat#240-B) at 10 ng/mL, anti-mouse/bovine/human transforming growth factor-β1 (R&D Systems, clone 1D11) at 75 μg/mL, recombinant mouse interleukin-10, (Pharmingen, cat#550070) at 3 μg/mL, and anti-mouse interleukin-10R (Pharmingen, clone 1B1.3a) at 50 μg/mL were utilized for in vitro CFSE assays and MLR.

Heterotopic Heart Transplantation

Cardiac allografts from BALB/c or C3H donor mice were transplanted heterotopically into B6 or B6 rag$^{-/-}$ recipients by standard microsurgical techniques. See, for example, Corry et al., in *Transplantation*, 1973, 16, 343-350. Allograft survival was assessed by daily palpation with rejection defined as loss of palpable beating that was confirmed at laparotomy. Survival differences were determined using Kaplan Meier Analysis via MedCalc statistical software.

Tissue Histological Examination

Transplanted hearts were fixed (10% formalin) and paraffin-embedded. Sections were cut (5 μm), deparaffinized, rehydrated, washed (1×PBS), and blocked for 1 hr in TSA blocking buffer. Primary antibody was mixed in TSA blocking buffer and sections were incubated (anti-GFP @ 1:1000, Acam ab6673) overnight. Sections were washed, incubated (1 hr) with the secondary antibody (Cy3 @ 1:250 in 1×PBS), washed and mounted (30% glycerin).

Results

Autologous CD117$^+$PC do not Enhance Recipient EC Chimerism, but Attenuate Acute Cardiac Allograft Rejection in a CD117-Dependent Manner A hypothesis that CD117$^+$PC would prolong cardiac allograft survival by increasing recipient EC chimerism was tested by determining the degree of initial allograft EC chimerism induced by autologous CD117$^+$PC transfer. Heart allografts were transplanted followed by host injection with 10$^7$ B6 CD117$^+$PC on day +1 (or received no treatment). Allografts were harvested on day +7 and analyzed by flow cytometry for relative host (H-2K$^d$) versus donor (H-2K$^b$) MHC class I expression by both CD31$^+$CD45$^-$ cells (putative EC) and CD31$^+$CD45$^+$ cells (putative CAC). This day 7 time point was chosen since it encompassed the time frame of combined ischemia-reperfusion-injury and early allo/innate-immune injury and as such represented a period in which potential signals for PC homing to the allograft vasculature were present. Additionally, this time point allowed assessment as to if recipient-type chimerism was still in place post-early inflammation (since recipient-type chimerism would have to survive this initial period of inflammation to potentially impact allograft survival). Interestingly, no significant increase in host-type chimerism was observed following CD117$^+$ PC transfer in either potential EC or CAC cell compartments. See FIG. 1.

Figure 2:
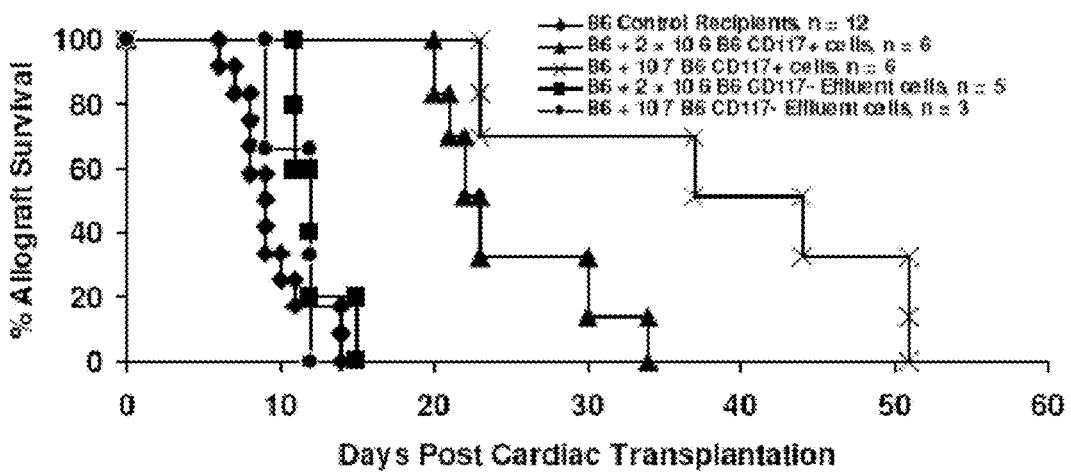
FIG. 2 is a graph showing dose-dependent survival prolongation with B6 CD117$^+$PC therapy and no benefit with CD117$^-$ effluent therapy.

In parallel, allograft recipients were treated with subsequent transfer of $2\times10^6$ or $10^7$ B6 CD117$^+$PC on day +1, +5, +9, and +15. As described above, CD117 was chosen as a PC marker since it's expression is required for homing to sites of ischemic injury and is frequently co-expressed on EPC as well as CAC. Additionally, freshly isolated CD117$^+$ cells were utilized to avoid bias toward any potential terminally-differentiated progenitor cell and to allow the allograft environment (ischemia-reperfusion and allo-immunity) to direct homing and differentiation in vivo. Subsequently, CD117$^+$PC infusions were administered through the estimated period of maximal ischemia-reperfusion-injury and acute allo-immune inflammation. Positive selection of CD117$^+$ donor bone marrow resulted in ≥80% CD117$^+$ donor cells. The CD117-depleted effluent cells were used as a control population (≤0.5% CD117$^+$). Results demonstrated pronounced dose-dependent allograft prolongation using autologous CD117$^+$PC therapy vs. controls (p<0.0002, FIG. 2). It was observed that allograft prolongation was CD117-dependent since CD117-depleted effluent cells did not prolong allograft survival versus controls (FIG. 2). These results indicate that despite a lack of potential recipient EC chimerism, autologous CD117$^+$PC therapy leads to dose-dependent cardiac allograft prolongation.

Autologous CD117$^+$PC Differenitally Engraft Cardiac Allografts and Peripheral Lymphoid Tissues Since allograft prolongation by autologous CD117$^+$PC was not associated with increased recipient EC chimerism, experiments were performed to determined whether CD117$^+$ PC localized in the allograft and/or lymphoid tissues. To accomplish this, B6GFP$^+$ transgenic mice were utilized as CD117$^+$PC cell donors. GFP$^+$CD117$^+$ cells ($10^7$) were injected RO on day +1 post-transplantation. On day +7, allografts and peripheral lymphoid-tissues were harvested for immunohistochemistry. Results showed that GFP$^+$ cells (PC-derived) were found in allografts in both peri-vascular and intra-luminal locations (data not shown).

Figure 3:
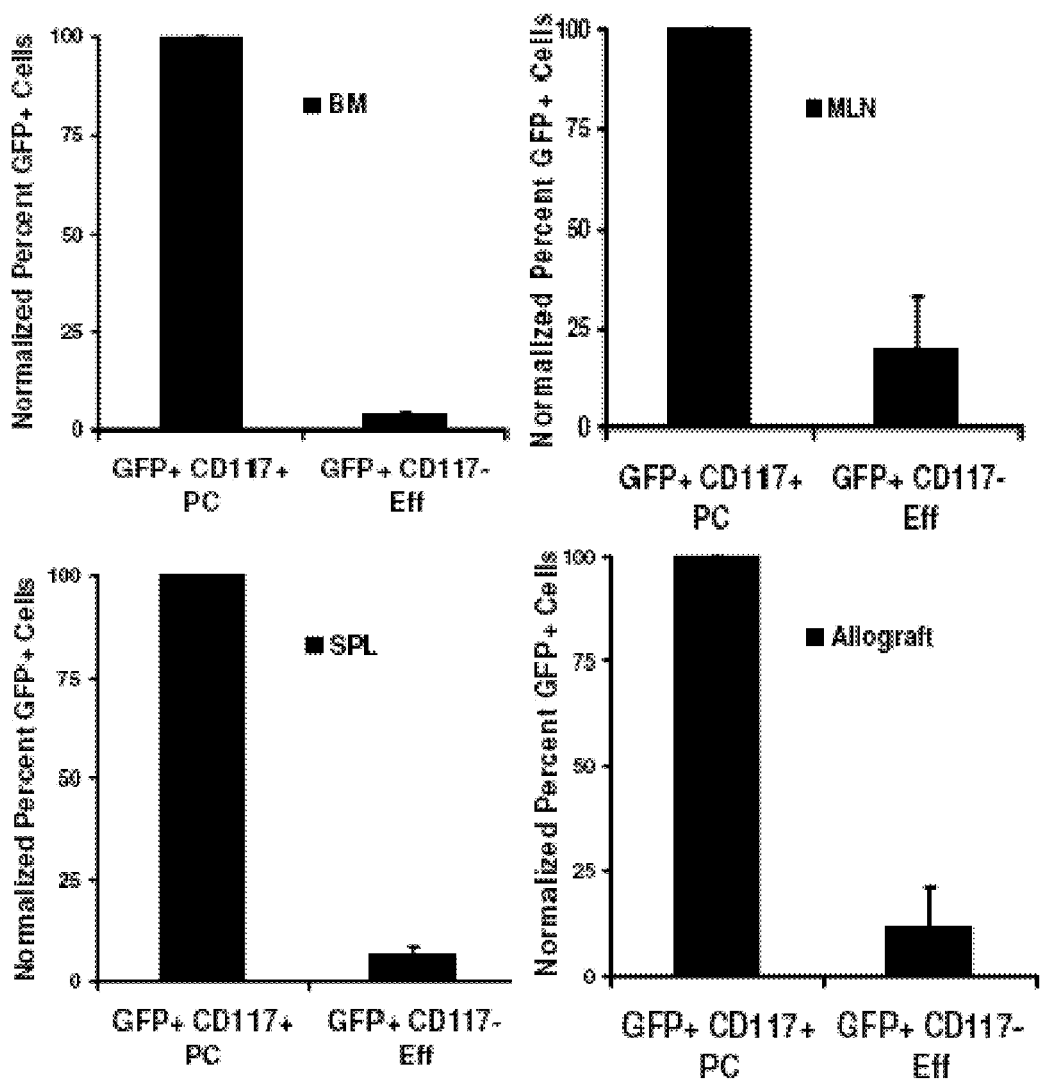
FIG. 3 is a graph of normalized summary data for paired triplicate experiments demonstrating significant differences in the BM, SPL, MLN, and allograft GFP$^+$ cellular content between paired GFP$^+$CD117$^+$ PC treated and GFP$^+$CD117$^-$ effluent treated heart transplant recipients. Results are normalized such that GFP$^+$CD17$^-$ effluent treated recipients are expressed as a percent of their corresponding GFP$^+$CD117$^+$ PC treated pair (n=3/group, p<0.001 for BM and SPL, p<0.01 for MLN and Allografts, paired T-tests).

To determine if the presence of GFP$^+$ cells in allografts and peripheral lymphoid tissues was due to specific 'trafficking' or 'homing' of progenitor cells versus random distribution, paired experiments were performed whereby BALB/c→B6 heart transplants were treated with $10^7$ GFP$^+$CD117$^+$PC or $10^7$ GFP$^+$CD117$^-$ effluent cells on day +1 (from the same cell donors to control for viability from a given cell prep). Allografts and peripheral lymphoid tissues were then analyzed by flow cytometry on day +7. Triplicate experiments demonstrated a large increase in the number of GFP$^+$ cells in the (SPL), mesenteric lymph nodes (MLN), and bone marrow (BM) when the transplant recipient received GFP$^+$CD117$^+$ PC as compared to recipients of GFP$^+$CD117$^-$ control cells in equivalent numbers (see FIG. 3), thus strongly suggesting that either 'homing' or increased survival of CD117$^+$PC-derived cells occurred at these sites of inflammation. Additionally, to assess if CD117$^+$PC-derived cells persisted in allografts, the distribution of GFP$^+$CD117$^+$PC and GFP$^+$CD117$^-$ effluent cells in the allografts and native hearts on day +15 post-transplantation (as CD117$^-$ control treated allografts all reject by day +15) were examined. Specifically, $10^7$ GFP$^+$CD117$^+$PC or $10^7$ GFP$^+$CD117$^-$ effluent cells were injected RO into recipients of BALB/c→B6 heart transplants on day +1. FACS analysis was then performed on allografts and native hearts on day +15. Data demonstrated similar numbers of GFP$^+$ cells between CD117$^-$ effluent treated allografts and native hearts (not shown). Additionally, the number of GFP$^+$ cells was similar between both effluent-treated groups (allografts and native hearts) and the CD117$^+$ PC-treated native heart (not shown). However, there was a large increase in the number of GFP$^+$ cells in the CD117$^+$PC treated allografts versus the native hearts. FACS analysis of allografts from BALB/c→B6 heart transplant recipients that received $2\times10^6$ GFP$^+$CD117$^+$PC on days +1, +5, +9, and +15 demonstrated GFP$^+$ cells (mean GFP expression 4%) at the time of rejection (n=4, time of rejection; day +20, +21, +30 and +35 respectively), whereas very little or no GFP$^+$ cells were found in the corresponding native hearts (<1%) (not shown).

Host-Derived CD117$^+$PC Vs Donor-Type Cells

Results indicated that allograft prolongation by CD117$^+$ PC is not related to MSC within the donor cell inoculum. That is, previous studies indicated that MSC are CD117$^-$CD45$^-$ whereas the cells used in this study are <0.5% CD117$^-$CD45$^-$. It was observed that host-type CD117$^-$ effluent cells, 30% of which are potential CD117$^-$CD45$^-$ MSC, did not prolong cardiac allografts (FIG. 2). Moreover, previous murine cardiac studies indicated that donor and recipient-type MSC are equally capable of promoting allograft survival, but only under either semi-allogeneic conditions or with concomitant sirolimus therapy. The present inventors have discovered that host-type CD117$^+$PC significantly prolonged allograft survival under fully allogeneic conditions (FIG. 2). Whether donor-type CD117$^+$PC would prolong cardiac allograft survival was also tested. Results showed that donor-type CD117$^+$PC resulted in modest allograft prolongation versus untreated controls (Table 1). However, donor-type CD117$^+$PC were significantly less effective than autologous cells for inducing allograft prolongation (Table 1).

TABLE 1

| Cell Type Infused | Day of Acute Rejection | Mean + SD | n |
|---|---|---|---|
| No Cells | 6, 7, 8 × 3, 9 × 3, 10, 11, 14 × 2 | 9.4 ± 2.5 days | 12 |
| Donor-Derived CD117+ PC ($10^7$) | 14, 16, 19 × 2<br>$p < 0.002$ | 17 ± 2.5 days<br>$p < 0.004$ | 4 |
| Host-Derived CD117+ PC ($10^7$) | 23 × 2, 37, 44, 51 × 2 | 38.2 ± 13 days<br>$p < 0.0002$ | 6 |

BALB/c→B6 heterotopic heart transplants were performed on day 0 with the subsequent retro-orbital injection of $10^7$ donor-derived BALB/c CD117$^+$PC on days +1, +5, +9, and +15. Allograft survival results were then compared to untreated controls and $10^7$ autologous B6 CD117$^+$PC treatment groups (seen in FIG. 2). Results demonstrate a modest prolongation of allograft survival versus controls (p < 0.004), whereas host-derived autologous CD117$^+$PC therapy resulted in robust allograft survival prolongation (p < 0.0002). Additionally, autologous CD117$^+$PC prolonged allograft survival significantly as compared to donor-derived therapy (p < 0.002, $10^7$ B6 CD117$^+$PC vs. $10^7$ BALB/c CD117$^+$PC). All survival differences were determined using Kaplan Meier Analysis.

Figure 4:
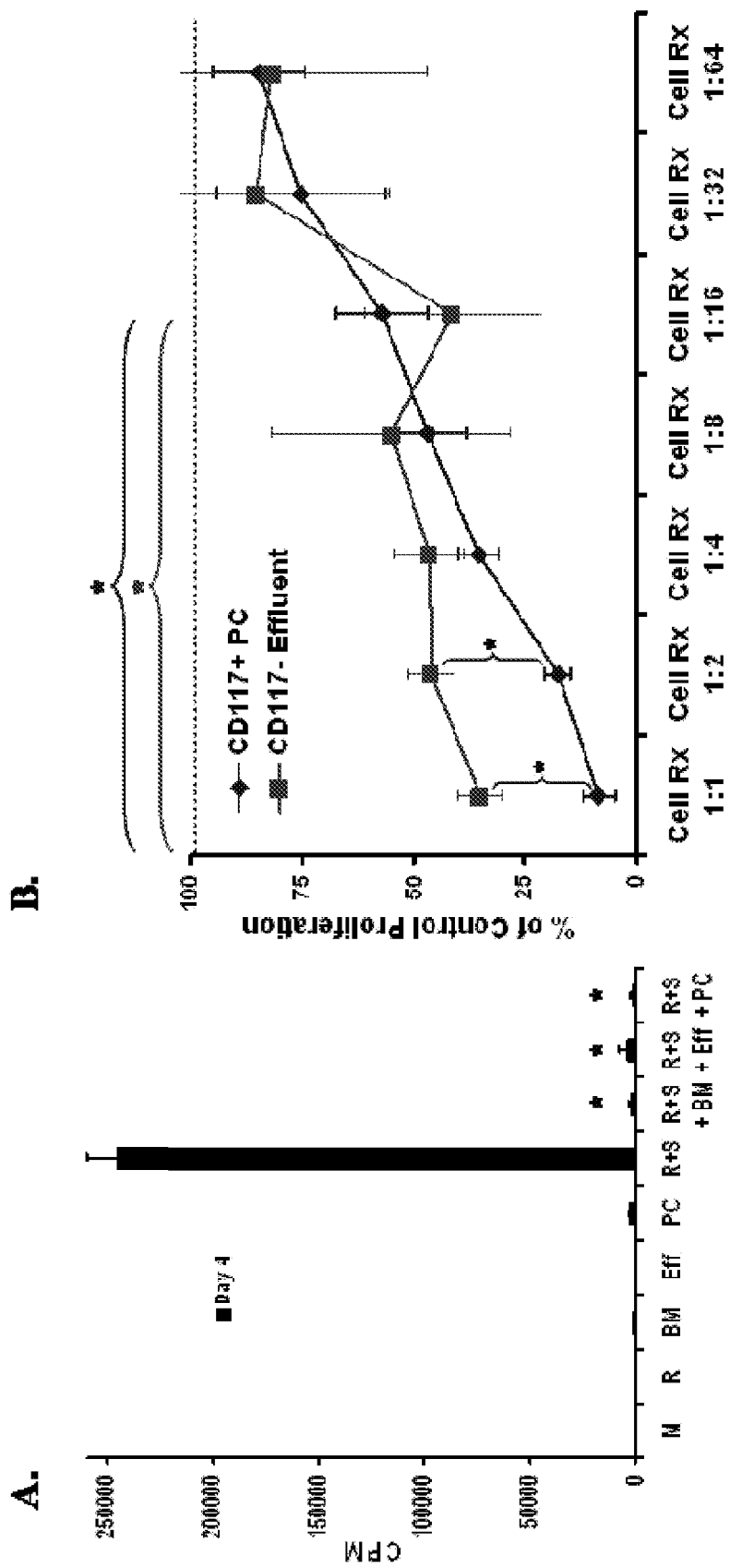
FIGS. 4A and 4B are graphs showing that autologous CD117$^+$ progenitor cells, CD117$^-$ effluent cells, and unmanipulated bone marrow cells equally inhibit in vitro T-cell proliferation. Standard mixed lymphocyte reactions (MLR) were set up using B6 lymph node cell responders (R) and γ-irradiated (2500 Rad) BALB/c splenocyte stimulators (S) in quadruplicate wells.
Figure 5:
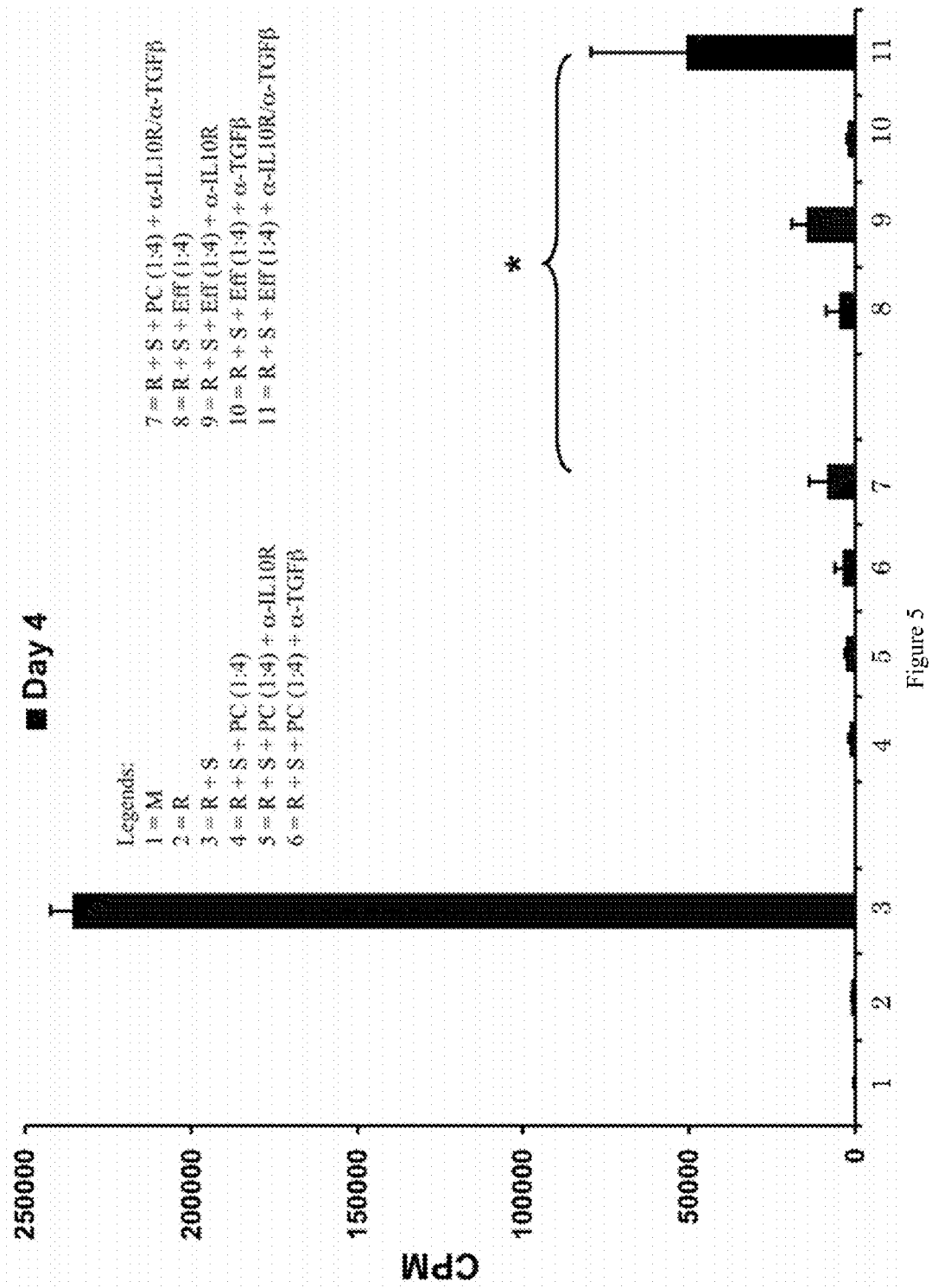
FIG. 5 is a bar graph showing combined antagonism of TGF-β and IL-10 did not significantly reverse inhibition of proliferation by CD117+PC, but modestly reversed inhibition of proliferation by CD117− effluent cells. Standard mixed lymphocyte reactions (MLR) were set up using B6 lymph node cell responders (R) and γ-irradiated (2500 Rad) BALB/c splenocyte stimulators (S) in quadruplicate wells. Freshly harvested host-type B6 CD117$^-$ effluent and host-type B6 CD117$^+$ progenitor cells (PC) were added to standard B6 responder (R)+BALB/c stimulator (S) cultures at 1:4 with responders. Anti-TGF-β at 75 μg/mL, anti-IL-10 Receptor (α-IL-10R) at 50 μg/mL, or the combination was added to the MLR culture in the indicated wells. No condition reversed inhibition of proliferation to control (R+S) levels. However, the combination of anti-IL-10 Receptor+Anti-TGF-β reversed inhibition of proliferation significantly better under CD117-effluent-treated conditions than under CD117+PC-treated conditions (*p<0.04, unpaired T-test). Error bars represent the standard deviation from quadruplicate wells in the MLR assay. Each experiment was repeated twice with the figure representing one typical result.

Both CD117+ and CD117-Depleted Bone Marrow Cells Inhibit Alloreactivity In Vitro As increased allograft survival with autologous CD117+ PC did not appear related to MSC, whether CD117+PC had unique immunomodulatory properties was investigated. Firstly, whether co-cultured B6CD117+PC, B6CD117− effluent cells and unmanipulated B6 BM cells (at 1:1 with responders) inhibited a standard MLR in vitro were determined. Results indicated that the addition of CD117+PC, as well as both control populations, strongly inhibited the proliferation of allo-specific T-cells (FIG. 4A). As inhibition of T-cell proliferation appeared to be non-specific, MLRs with paired dilutions of both CD117+PC and CD117− effluent cells (1:1-1:256) were performed to determine if there existed a difference in the potency of inhibition between the two cellular populations. Results indicated that CD117+PC inhibited T-cell proliferation significantly better than CD117− effluent cells at high ratios with responder T-cells (out to 1:2, $p<0.0002$, unpaired T-test), but that there was no significant difference in their abilities to inhibit T-cell proliferation out beyond 1:2 (FIG. 4B). It was observed that significant in vitro T-cell inhibition by both CD117+PC and CD117− effluent was lost at 1:32 with responders (FIG. 4B). Given these results, the present inventors next sought to elucidate if the inhibitory effect of CD117+PC or other BM populations on T-cell proliferation was contact-dependent and/or paracrine in vitro. To accomplish this, in vitro CFSE proliferation assays were performed utilizing transwell culture plates. Results indicated that co-culture with either CD117+ or CD117-depleted (effluent) BM-derived cells resulted primarily in profound paracrine inhibition of alloreactive T-cells (data not shown). Combined inhibition of TGF-β and IL-10 resulted in moderate reversal of T-cell inhibition by B6 CD117−effluent but not B6 CD117+PC (FIG. 5), suggesting a potential parallel pathway between TGF-β and IL-10 for in vitro inhibition of T-cell proliferation by control CD117− effluent cells. However, without being bound by any theory, IL-10 and TGF-β do not appear to be significantly involved mechanistically for in vitro inhibition of T-cell proliferation by CD117+PC.

The effect of CD117+PC on in vivo T-cell inhibition was also examined. CFSE-labeled B6CD45.1 splenocytes ($10^7$) were injected RO on day 0 relative to BALB/c→B6 heart transplantation. On day +1, $10^7$ B6 CD117+PC or $10^7$ B6 CD117− effluent cells were injected RO in experimental animals (paired control recipients were left untreated). Results showed no statistically significant difference in T-cell proliferation in the MLN, SPL, or allograft in CD117+PC treated or CD117− effluent treated allograft recipients (not shown).

As previous studies have demonstrated donor-type MSC to increase CD4+CD25+Foxp3+ regulatory T-cells (Tregs) in vivo, experiments were performed to determined if CD117+ PC treatment also led to an increase in Tregs. BALB/c→B6 heart transplant recipients received $10^7$ B6 CD117+PC (or no cells) RO on day +1 and were sacrificed on day +7 for analysis. Results indicated no statistically significant increase in CD4+CD25+Foxp3+ Tregs in any compartment (not shown). BALB/c→B6 heart transplant recipients that received $10^7$ B6 CD117+PC on days +1, +5, +10, and +15 were also analyzed at the time of rejection and found no significant increase in Tregs in any compartment out to >50 days post transplantation (not shown).

Autologous CD117+PC Therapy

Figure 6:
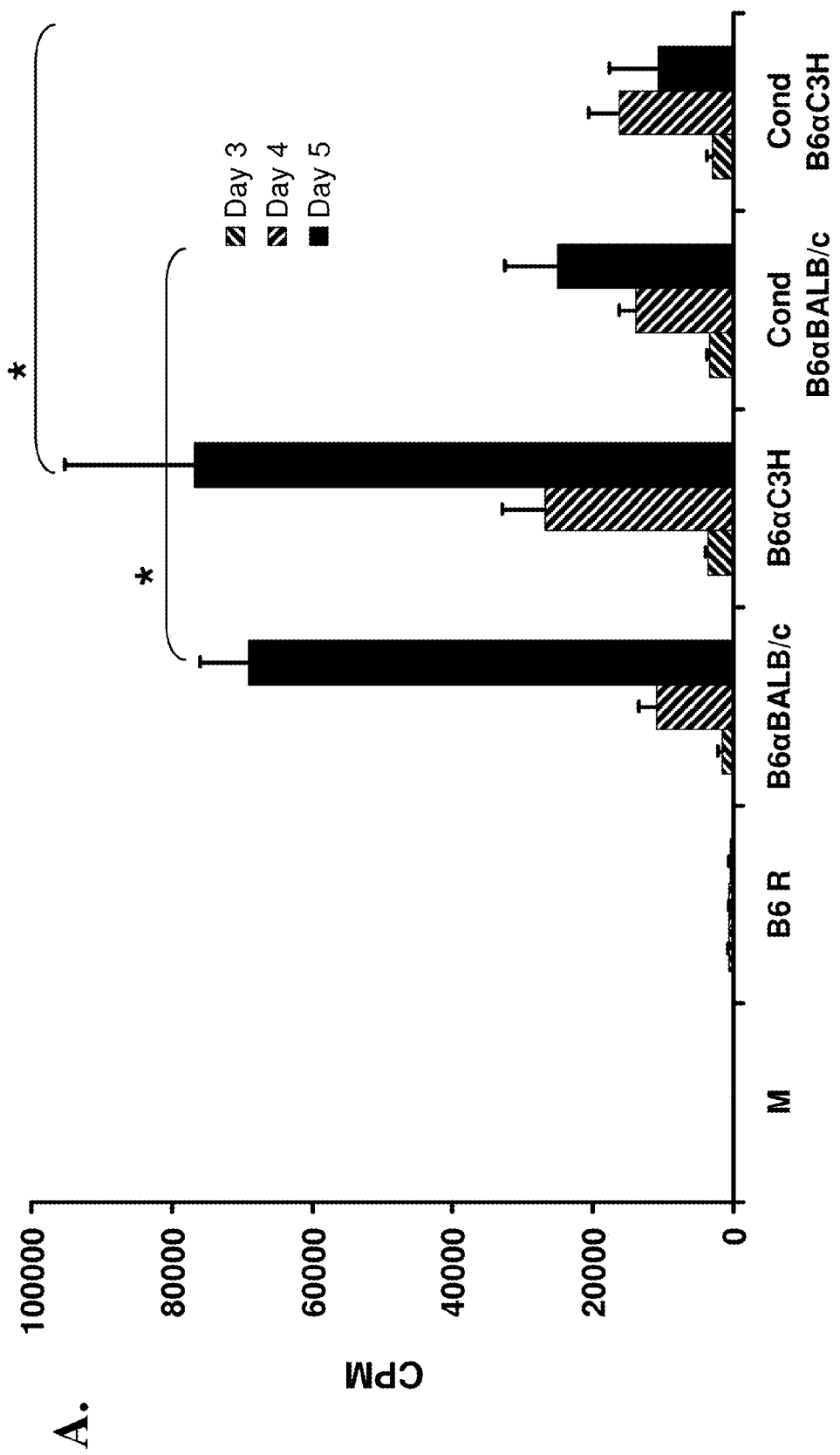
FIG. 6 is a graph showing that conditioned splenocytes are non-specifically hyporesponsive upon re-stimulation ex vivo. Splenocytes, taken from B6 recipients of BALB/c heart allografts surviving >30 days conditioned by treatment with $10^7$ B6 CD117$^+$PC on days +1, +5, +9, and +15, were re-stimulated ex-vivo via standard MLR. Results demonstrate a blunted proliferative response of conditioned B6 splenocytes against both donor-type BALB/c and third party C3H stimulators versus naïve control B6 responders (p<0.001 conditioned B6αBALB/c vs. naïve B6αBALB/c and p<0.01 conditioned B6αC3H vs. naïve B6αC3H, unpaired T-test).

Given that CD117+PC were shown to inhibit T-cell proliferation in vitro, yet did not significantly effect early T-cell proliferation in vivo, experiments were conducted to determine if autologous CD117+PC effect the late responsiveness of T-cells restimulated ex-vivo. To accomplish this, conditioned splenocytes, from recipients of BALB/c→B6 heart transplants that received $10^7$ autologous CD117+PC on days +1, +5, +9, and +15 and whose allografts survived >30 days, were harvested and utilized for in vitro re-stimulation experiments. Results showed a non-specific blunting of the conditioned T-cell proliferative response to both BALB/c and third party C3H stimulators compared to controls (FIG. 6).

Discussion

The need for alternative therapies in transplantation of cells, tissues, and organs has been obvious for quite some time. Despite standard immunosuppression, rates of acute and chronic rejection, and as a consequence survival, have not been satisfactory. Unfortunately, new therapies for allograft prolongation in humans have been mostly unsuccessful, in part due to the fact that many of these therapies rely on T-cell dependent mechanisms including regulatory T-cells (Tregs). A significant obstacle has been the fact that standard immunosuppression with CNI is inhibitory to T-cells—both effector and regulatory. Recently, donor-specific bone marrow transplantation (BMT) has demonstrated tolerance induction in animal models and humans. However, this therapy is donor-derived and therefore carries the risk of graft versus host disease (GVHD), as well as other serious immune reactions.

The present inventors have discovered that autologous therapy form an attractive safe alternative to donor cell therapy. In two studies, autologous MSC were used to treat fully allogeneic cardiac allografts with no allograft prolongation seen in the first (Casiraghi et al., *J. Immunol.*, 2008, 181, 3933-3946) and robust prolongation only with concomitant Sirolimus therapy in the second (Ge et al., *Am J Transplant*, 2009, 9, 1760-1772). Studies with donor-derived MSC also demonstrate an increase in CD4+CD25+Foxp3+ Tregs, which was interpreted as indicating that there may be a mechanistic requirement for Tregs in tolerance induction by MSC (Casiraghi et al., *J. Immunol.*, 2008, 181, 3933-3946). If true, this would make co-therapy with CNI potentially detrimental to the efficacy of donor-derived MSC, thus further limiting potential clinical utility.

The present inventors investigated an entirely different autologous progenitor cell population with the belief that it is possible attain allograft prolongation without GVHD or Treg dependence. Without being bound by any theory, it was believed that CD117+PC would differentiate into vascular cells and incorporate into ischemia-reperfusion/allo-immune injured intra-graft vessels, thus 'hiding' the allograft by limiting the primary target of the acute alloresponse.

Results showed significant dose-dependent, CD117-dependent cardiac allograft prolongation by CD117+PC despite a lack of any significant increase in recipient vascular chimerism. CD117+PC differentially engrafted cardiac allografts and peripheral lymphoid tissues in vivo and significantly inhibited T-cell proliferation in vitro. However, in vitro results demonstrated relatively equal inhibition of T-cell proliferation by autologous CD117+PC, CD117− effluent cells, and unmanipulated BM cells, indicating that multiple BM populations can inhibit T-cell proliferation in vitro. Interestingly, neither CD117+PC nor CD117− effluent cells significantly effected early T-cell proliferation in vivo. Despite this, recipient splenocytes, conditioned by CD117+PC and prolonged exposure to BALB/c allografts, were significantly diminished in their proliferative capacity to ex-vivo re-stimulation with donor-type and third party allo-APCs, suggesting CD117+PC lead to a dampened or 'sluggish' late cellular allo-immune response. One possibility for this observation is that CD117+PC may be acting to support the survival of certain parenchymal cells/tissues under conditions of oxidative and/or inflammatory stress (possibly by dampening inflammation).

A possibility of a small number of contaminating MSC being responsible for allograft prolongation (<0.5% of the $CD117^+PC$ prep is $CD117^-CD45^-$) was eliminated by distinguishing $CD117^+PC$ from MSC in a variety of ways. Therapy with CD117-depleted (effluent) cells which contain 30% $CD117^-CD45^-$ cells (potential source of MSCs), did not lead to increased cardiac allograft survival, thus arguing against a contribution by MSC and demonstrating a requirement for CD117 expression. Additionally, $CD117^+PC$ therapy did not lead to an increase in $CD4^+CD25^+Foxp3^+$ Tregs as seen with MSC therapy. This observation does not preclude a functional requirement for Tregs by $CD117^+PC$ (or for MSC), but does further distinguish $CD117^+PC$ from MSC. It is clear that $CD117^+PC$ represent a unique progenitor cell population that is distinct from MSC.

Results of these studies demonstrate the novel finding that autologous $CD117^+PC$ abrogate acute cardiac allograft rejection in a dose-dependent, CD117-dependent fashion and that the allograft promoting effects are unique from those of MSC. As autologous cells, $CD117^+PC$ pose no significant risk to the host and can be applied to human transplantation. Without being bound by any theory, it is believed that $CD117^+PC$ reduces local inflammation and promotes the survival of parenchymal cells under duress. In some embodiments, $CD117^+PC$ can be used as a co-therapeutic with tolerance promoting agents to facilitate tolerance induction or to facilitate engraftment of other cellular therapeutics in humans (i.e., islet transplantation) by transiently dampening inflammation or promoting the survival of cells under stress.

Islet Cell Transplantation

One of the primary barriers to islet transplant success is the early loss of graft tissue following implantation. Also, there is an ongoing need for novel and safe therapies that can inhibit graft rejection and/or autoimmune-mediated islet injury. This experiment is the serendipitous result of the unexpected capacity of systemically administered autologous CD45+ CD117+ bone marrow (BM)-derived cells to significantly prolong cardiac allograft survival (see above). These cells appear to contrast sharply with features of BM-derived mesenchymal stem cells. This experiment illustrates the capacity of autologous CD45+CD117+ BM derived stem cells to promote islet engraftment and/or allograft survival.

Type 1 Diabetes

It should be appreciated that the BM-derived cells used in some aspects of the present invention are distinguished from mesenchymal stem cells. BM-derived progenitor cells (PC) can give rise to multiple cellular lineages—including ECs, smooth muscle cells, adipocytes, and hematopoietic cells— and are identified by the cell surface marker c-kit (CD117). C-kit+ cells have been demonstrated to contain cellular subpopulations that are CD34+CD45− and CD34+/−CD45+ and therefore have the potential capacity to give rise to both EPC and CAC populations. Co-expression of c-kit on vascular progenitors is critical for homing to injured vasculature during neo-angiogenesis and repair. It is also worth noting that in addition to being expressed on many angiogenic progenitor cells, c-kit is also considered a primary marker for hematopoietic stem cells (HSC). This is in direct contrast to that of mesenchymal stem cells (MSC), which are usually considered CD117−CD45− and have been found to inhibit allo T-cell proliferation as well as promote cardiac allograft tolerance in a donor-derived form. Unfortunately, primary autologous MSC therapy has been ineffectual in promoting allograft survival. Such results are essentially the opposite of what we find with the proposed CD45+CD117+ BM population. This experiment determines whether autologous BM-derived CD117+ cells that are considered to be putative EPC can facilitate islet engraftment and/or islet allograft prolongation. BM-derived CD117+ cells are useful as an adjunct therapy to promote islet transplant engraftment.

For the purpose of studying islet function in mice, it was found that the recently developed akita mouse model to be highly useful for studying islet graft function. The 'akita' polymorphism is a transition mutation of the mouse insulin 2 gene (Ins 2). Although mice have two function insulin genes, the akita mutation results protein misfolding such that the akita-Ins2 acts as a 'dominant negative' of insulin granule formation and vastly reduced insulin secretion. Thus, the akita genotype results in a non-autoimmune, MODY (maturity onset diabetes of the young) phenotype. This autosomal dominant gene results in durable and irreversible hyperglycemia (>450-600 mg/dl). The level of hyperglycemia is quite persistent in akita mice relative to SZ-induced B6 mice. Also, akita recipients accept wild-type syngeneic islet grafts, indicating that this is a non-autoimmune form of disease. In addition, akita mice acutely reject islet allografts indicating that these are immune-competent mice capable of mounting alloimmune responses. Based on these findings, the akita mouse is used as a model to determine the ability of autologous CD45+CD117+ BM-derived cells to promote islet engraftment and/or allograft prolongation.

Islet Engraftment Enhancement Experiment

Graded (i.e., minimal) numbers of wild-type syngeneic B6 islets are transplanted in spontaneously diabetic male B6 akita recipient mice in the presence or absence of positively selected, autologous CD45+CD117+ BM-derived cells. These cells are administered systemically or co-transplanted with the islet graft beneath the kidney capsule. Limiting numbers of wild-type B6 islets (empirically determined from approximately 100-300 islets) are transplanted according to the following groups:

| Co-transplanted BM cells | Route of BM cell transfer | Purpose |
| --- | --- | --- |
| None | | Control |
| B6 (syngeneic) CD117+ BM | systemic (i.v.) | Test Group |
| B6 CD117+ BM cells | co-transplanted | Test Group (for increased efficacy) |
| B6 CD117-depleted BM cells | systemically or co-transplanted | Control for BM cell type |
| B6 CD117+ BM, no islet graft | systemically or co-transplanted | Impact of BM cells on diabetes itself |

This experiment is used to determine whether co-administered autologous CD117+ BM cells improve islet engraftment as defined by a reduced number of syngeneic islets required for successful achievement of euglycemia. Islet function is monitored longitudinally (≥100 days) to ensure robust islet function. In addition, systemic delivery of BM cells is compared with local co-transplantation with the islets to determine if the local graft micro-environment is a benefit or detriment to graft function. Observation that reduced numbers of islets are required to restore euglycemia in the presence of BM cells, indicates that CD117+ cells can improve islet engraftment.

Islet Allograft Survival Experiment

The CD117+ cells can have a benefit for promoting islet allograft survival in akita recipients. This experiment determines if the survival of a therapeutic islet allograft (e.g., 400 allogeneic BALB/c islets) is prolonged in the presence of co-administered autologous CD117+ BM cells. The following experimental groups are used:

| Co-transplanted BM cells | Route of BM cell transfer | Purpose |
| --- | --- | --- |
| None | | Control |
| B6 (syngeneic) CD117+ BM | systemic (i.v.) | Test Group |
| B6 CD117+ BM cells | co-transplanted | Test Group (for increased efficacy) |
| B6 CD117-depleted BM cells | systemically or co-transplanted | Control for BM cell typeB6 CD117+ |
| BALB/c (donor) BM cells | systemically or co-transplanted | Test for host versus donor requirement |

This experiment shows that host but not donor type BM cells promote islet allograft prolongation. This experiment is also used to determine whether local (i.e., co-transplantation) of BM cells is superior to systemic administration. This experiment shows that CD117+ cells are capable of extending islet allograft survival.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for improving the transplantation outcome in a mammalian cell, tissue, or organ transplant recipient, said method comprising administering to said mammalian transplant recipient a therapeutically effective amount of unmanipulated bone marrow derived autologous CD117+ cells.

2. The method of claim 1, wherein autologous CD117+ cells comprise autologous CD117+ progenitor cells, autologous CD117+ stem cells, or a mixture thereof.

3. The method of claim 2, wherein autologous CD117+ cells are autologous CD117+ progenitor cells.

4. The method of claim 3, wherein autologous CD117+ progenitor cells are bone marrow derived autologous CD117+ progenitor cells.

5. The method of claim 1, wherein autologous CD117+ cells are autologous CD45+CD117+ cells.

6. The method of claim 1, wherein said improvement in transplantation outcome is reduced graft rejection.

7. The method of claim 1, wherein said improvement in transplantation outcome is increased graft survival.

8. The method of claim 1, wherein said transplantation comprises transplantation of heart, islet cells, kidney, liver, lung, pancreas, skin, ocular, intestine, or a combination thereof.

9. The method of claim 8, wherein said transplantation comprises islet cell grafting.

10. The method of claim 1 further comprising administering a therapeutically effective amount of an immunosuppressive agent to said mammalian transplant recipient.

11. The method of claim 10, wherein said therapeutically effective amount of said immunosuppressive agent is reduced as compared to a therapeutically effective amount of said immunosuppressive agent alone.

12. The method of claim 10, wherein said immunosuppressive agent is cyclosporin A, rapamycin, FK501, mycophenolate mofetil, azathioprine, deoxyspergualin, FK506, (tacrolimus), cytoxan (cyclophosphamide), everolimus, glucocorticoid steroids (prednisone/solumedrol), or a combination thereof.

13. The method of claim 10, wherein the immunosuppressive agent is a cyclic peptide produced by the fungus species *Tolypocladium Inflatum* Gams.

14. The method of claim 13, wherein the immunosuppressive agent is cyclosporin A.

15. The method of claim 1, wherein said improvement in transplantation outcome is decreased lymphocytic infiltration, vasculitis, infarction, ischemia, thrombosis, intimal thickening, glomerular atrophy, glomerular sclerosis, tubular atrophy, hyalinization, interstitial fibrosis, cortical fibrosis, serum creatinine levels, intimal proliferation, hypertrophy, cardiac vessel disease post-transplant, graft intimal hyperplasia, luminal occlusion, or bronchitis obliterans.

16. The method of claim 1, wherein autologous CD117+ cells are co-transplanted, administered systemically or a combination thereof.

* * * * *